(12) United States Patent
Henkelmann et al.

(10) Patent No.: US 6,479,687 B2
(45) Date of Patent: Nov. 12, 2002

(54) PREPARATION OF VINYLPHOSPHONIC ACID COMPOUNDS

(75) Inventors: Jochem Henkelmann, Mannheim (DE); Thomas Preiss, Weisenheim am Sand (DE); Arnd Böttcher, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/803,146

(22) Filed: Mar. 12, 2001

(65) Prior Publication Data

US 2002/0004607 A1 Jan. 10, 2002

Related U.S. Application Data

(63) Continuation-in-part of application No. 09/402,832, filed on Oct. 13, 1999, now abandoned, and a continuation of application No. PCT/EP98/02037, filed on Apr. 8, 1998.

(30) Foreign Application Priority Data

Apr. 15, 1997 (DE) .......................... 197 15 667

(51) Int. Cl.[7] ................................. C07F 9/40
(52) U.S. Cl. ....................................... 558/142
(58) Field of Search .................. 558/87, 142

(56) References Cited

U.S. PATENT DOCUMENTS

| | | | |
|---|---|---|---|
| 3,673,285 A | | 6/1972 | Lin |
| 3,681,481 A | | 8/1972 | Lin |
| 4,115,482 A | * | 9/1978 | Oswald et al. ............ 260/975 |
| 4,198,354 A | * | 4/1980 | Schrepfer et al. .......... 260/968 |
| 4,670,193 A | * | 6/1987 | Thottathil et al. ......... 558/132 |
| 5,693,826 A | | 12/1997 | Tanaka |

OTHER PUBLICATIONS

Organometallics 1996, 15, 3259–3261, Han et al.
J.Am.Chem.Soc., 118, 1996, 1571–1572.

* cited by examiner

*Primary Examiner*—Joseph K. McKane
*Assistant Examiner*—Golam M.M. Shameem
(74) *Attorney, Agent, or Firm*—Keil & Weinkauf

(57) ABSTRACT

A process for preparing vinylphosphonic acid compounds of the formula (I)

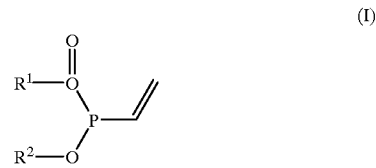

where $R^1$ and $R^2$ are, independently, H, $C_{1-16}$-alkyl, $C_{6-12}$-aryl, $C_{7-12}$-alkaryl or $C_{7-12}$-aralkyl, it being possible for the organic radicals to be substituted by one or more halogen atoms, hydroxyl, acyl or acetoxy groups, by reacting phosphorous acid compounds of the formula (II)

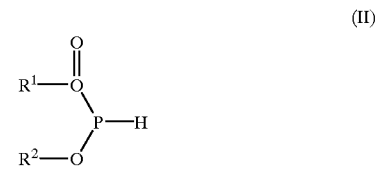

with acetylene in the presence of a Pd(O) complex or Pt(O) complex as catalyst.

7 Claims, No Drawings

PREPARATION OF VINYLPHOSPHONIC ACID COMPOUNDS

This application is a CIP of Ser. No. 09/402,832 filed on Oct. 13, 1999, now abandoned and a continuation of PCT/EP98/02037 filed Apr. 8, 1998.

The present invention relates to a process for preparing vinylphosphonic acid compounds using Pd(0)-catalysts, and to the use of such catalysts for the preparation process.

Vinylphosphonic acid compounds, in particular dialkyl vinylphosphonates, have importance as precursors for preparing vinylphosphonic acid and as monomers for copolymerization for producing adhesives or flame-resistant plastics.

Various processes for preparing them are known. In the process described in DE-C21 32 962, ethylene oxide is reacted with phosphorus trichloride to give 2-chloroethanephosphonic dichloride, and this compound is converted into bis-2-chloroethyl 2-chloroethanephosphonate. The resulting compound is then reacted with phosgene in the presence of a catalyst. Amines, heterocyclic nitrogen compounds, as well as tertiary phosphines, are used as catalyst.

DE-A-30 01 894 describes a process for preparing vinylphosphonic acid derivatives, in which dialkyl 2-acetoxyethanephosphonates are cleaved in the presence of acidic or basic catalysts. The basic catalysts proposed are tertiary amines and phosphines, as well as ammonium salts or phosphonium salts, besides heterocyclic compounds and amides. The disadvantage of the process is the formation of a mixture of vinylphosphonic acid derivatives. The maximum content of dialkyl vinylphosphonates is 23%.

An improved variant of this process discolosed in DE-A-31 20 437 entails a distillation followed by reaction of the bottom product mixture resulting from the distillation with orthocarboxylates to give dialkyl vinylphosphonates.

EP-A-0 722 948 discloses thermal cleavage of diethyl 2-acetoxyethanephosphonate in the gas phase to give acetic acid and dimethyl vinylphosphonate. No catalyst is used in this case.

The disadvantages of the above processes are the formation of product mixtures, elaborate, multistage synthetic processes, the need to use high reaction temperatures, and the use of chlorinated starting compounds. The large proportion in particular considerably impairs the economics of the process.

A simple addition reaction is advantageous for synthesizing vinylphosphonic acid compounds and results in the required product in high yields. One example of a reaction of this type is addition of dialkyl phosphites onto acetylene. U.S. Pat. No. 3,673,285 describes the addition of alkynes onto diethyl phosphite at from 130 to 200° C. in the presence of nickelphosphine complexes. On addition of acetylene, the corresponding diethyl vinylphosphonate is obtained in a yield of 30%. The disadvantage of this process is, besides the low yield, the tendency of the phosphorous esters to decompose in a strongly exothermic reaction at temperatures as low as 130° C.

It is an object of the present invention to provide a process for preparing vinylphosphonic acid compounds which avoids the disadvantages of known processes and makes the required products available with high selectivity and yield under mild conditions from acetylene and phosphorous acid compounds.

We have found that his object is achieved by a process for preparing vinylphosphonic acid compounds of the formula (I)

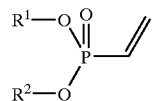

where $R^1$ and $R^2$ are, independently, H, $C_{1-16}$-alkyl, $C_{6-12}$-aryl, $C_{7-12}$-alkaryl or $C_{7-12}$-aralkyl, it being possible for the organic radicals to be substituted by one or more halogen atoms, hydroxyl, acyl or acetoxy groups, by reacting phosphorous acid compounds of the formula (II)

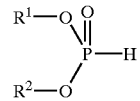

where $R^1$ and $R^2$ have the above meaning, with acetylene in the presence of a Pd(0) complex or a Pt(0) complex as catalyst.

We have found that the reaction of acetylene wit phosphorous acid compounds, in particular dialkyl phosphites, to give vinylphosphonic acid compounds, in particular dialkyl vinylphosphonates, is possible with high selectivity and yield by using a catalytic amount of a Pd(0) or Pt(0) complex, preferably Pd(0) complex, especially in homogeneous phase. Palladium complexes have been used for hydrophosphorylation of terminal higher alkynes such as 1-octyne, see J. Am. Chem. Soc., 118 (1996) 1571–1572. However, reaction with acetylene is not mentioned or proposed here.

The hydrophosphorylation of higher alkynes and also of acetylene is disclosed in U.S. Pat. No. 5,693,826. According to this reference, various Pd(II) and Pd(0) complexes can be used as catalyst. In the examples of this reference, there is made use of Pd(II) complexes exclusively, with 2 exceptions. These show that Pd(0) complexes give lower yields and require longer reaction times, respectively, compared to Pd(II) complexes. When acetylene is used as a starting product, the yields are very low (20%).

We have now found that acetylene can be reacted under very mild conditions with very high selectivity using a Pd(0) catalyst to give vinylphosphonic acid compounds, in particular dialkyl vinylphosphonates, directly without any dimerization, oligomerization or polymerization of acetylene or double reaction to give a tetraalkyl ethylenediphosphonate.

It is supposed that the low yield mentioned above is due to one or several of these side reactions occurring while the hydrophosphorylation reaction is carried out. Acetylene can be said to have a different reactivity, compared to substituted acetylenes like, for example, 1-octyne. When Pd(0) complexes are used in the hydrophosphorylation reaction, is as surprisingly found that high conversion and high selectivities could be obtained, contrary to the use of Pd(II) complexes.

In the phosphorous acid compounds of the formula (II) employed for the reaction, $R^1$ and $R^2$ are, independently, H, $C_{1-16}$-alkyl, $C_{6-12}$-aryl, $C_{7-12}$-alkaryl or $C_{7-12}$-aralkyl, it being possible for the organic radicals to be substituted by one or more halogen atoms, hydroxyl, acyl or acetoxy groups. $R^1$ and $R^2$ are preferably, independently, linear $C_{1-12}$-alkyl, phenyl, ($C_{1-6}$-alkyl)phenyl or phenyl($C_{1-6}$-alkyl).

$R^1$ and $R^2$ are particularly preferable, independently, linear $C_{1-6}$-alkyl radicals. These radicals are preferably unsubstituted.

If $R^1$ and $R^2$ differ from hydrogen, the compounds employed are diesters of phosphorous acid. Reaction thereof results in diesters of vinylphosphonic acid of formula (I). This reaction can be followed by cleavage of the ester groups, resulting in vinylphosphonic acid, $R^1OH$ and $R^2OH$.

Conversion of the phosphorous acid compounds into the vinylphosphonic acid compounds takes place in the presence of a Pd(0) complex or Pt(0) complex, but preferably Pd complex as catalyst. The catalyst is usually present in homogeneous phase for this purpose.

The Pd(0) complex employed preferably has phosphine ligands or phosphite ligands. A large number of ligands are suitable as phosphine ligands or phosphite ligands. For example, the ligands may have the formula PXYZ where X, Y and Z are, independently, alkyl, aryl, alkoxy or aryloxy radicals having up to 18 carbon atoms. Alkyl or aryl radicals are preferred in this connection, especially aryl radicals. Corresponding ligands are described, for example, in DE-A.1 593 277. They are preferably triarylphosphines or triaryl phosphites in which the aryl groups are unsubstituted or substituted. Suitable substituents are $C_{1-6}$-alkyl, acyl or acetoxy radicals. The triarylphosphine or triarylphosphite is preferably unsubsituted. Triphenylphosphine is particularly employed as phosphine ligand. The catalyst used particularly preferably according to the invention is tetrakis (triphenylphosphine)palladium(0).

The complexes may be composed, for example, of monodentate or bidentate ligands. Examples of a suitable complex structure is the following:

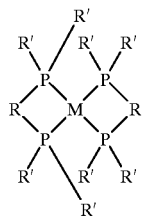

where the meanings are

M Pd, Pt, preferably Pd

R independently at each position organic radicals linked via O and/or C atoms to the phosphorus atoms, in particular aryl radicals or aryloxy radicals having 2 sites capable of linkage.

$R^1$ independently at each position monovalent organic radicals, in particular aryl and/or aryloxy radicals.

It is preferred for the monovalent radicals to be derived from benzene or phenol and for the divalent radicals to be derived from biphenyl, 1,1'-binaphthyl, biphenyloxy and/or 1,1'-binaphthyloxy radicals. It is moreover possible for all the aromatic radicals to be substituted, for example by one or more $C_{1-6}$-alkyl radicals or corresponding alkoxy radicals. The biphenyl and binaphthyl radicals, and radicals derived therefrom, are linked to the phosphorus atom via 2 positions in the molecule. It is possible for both positions to be linked to the same phosphorus atom. It is also possible for them to be linked to different phosphorus atoms and thus produce bridged structures which have, for example, 2 phosphorus atoms and 3 of said radicals. Suitable corresponding bidentate phosphite ligands are described in U.S. Pat. No. 5,512,695. The phosphite ligands described therein can also be employed in analogous form as phosphine ligands. Further suitable monodentate and bidentate aromatic ligands are described in WO 95/29153. The described ligands can in this case likewise be employed as phosphine or phosphite ligands.

The catalysts can moreover be formed in situ in the reaction.

The catalysts employed according to the invention are normally employed in an amount of from 0.01 to 10% by weight, preferably in an amount of from 0.5 to 3% by weight, particularly preferably 1 to 2% by weight, based on the amount of phosphorous acid compounds to be vinylated, in particular dialkyl phosphites.

The temperature in the reaction is, as a rule, from 20 to 120° C., preferable 20 to 80° C., particularly preferably 60 to 80° C.

The reaction can moreover be carried out without solvent or in the presence of an inert solvent. Examplex of inert solvents which can be used are cyclic ethers such as THF, long-chain ethers such as triethylene glycol dimethyl ether or tetraethylene glycol dimethyl ether.

The reaction is carried out under atmospheric pressure or elevated pressure, preferably at from 1 to 20, particularly preferably 1.5 to 6, bar (absolute). This preferably entails mixing the phosphorous acid compound of the formula (II) and the catalyst, and passing in acetylene. Once the reaction is complete, the product can be removed by distillation.

The novel process can be carried out continuously or batchwise.

The invention also relates to the use of the catalysts described above in the preparation of vinylphosphonic acid compounds, in particular vinylphosphonic esters, specifically dialkyl vinylphosphonates.

The invention is explained in details by means of Examples shown hereafter.

EXAMPLE 1

6 g of dimethyl phosphite were stirred with 20 ml of tetrahydrofuran in a 4-neck flask which had a capacity of 500 ml and was equipped with an internal thermometer, dry-ice condenser and gas introduction tube, and were degassed under argon. After addition of 2 mol % tetrakis-(triphenylphosphine)palladium(0), 6 l/h acetylene were passed into the reaction solution at 60° C. for 24 h. Dimethyl vinylphosphonate was isolated in 90% yield after workup by distillation.

EXAMPLE 2

25 g of diethyl phosphite were degassed under argon while stirring in a 4-neck flask which had a capacity of 500 ml and was equipped with an internal thermometer, dry-ice condenser and gas introduction tube. After addition of 1 mol % tetrakis(triphenylphosphine)palladium(0), 6 l/h acetylene were passed into the reaction solution at 60° C. for 24 h. Diethyl vinylphosphonate was isolated in 95% yield after workup by distillation.

EXAMPLE 3

65 g of dimethyl phosphite were stirred with 110 ml of tetrahydrofuran in an autoclave with a capacity of 300 ml. After addition of 0.7 mol % tetrakis(triphenylphosphine) palladium(0), initially 5 bar of nitrogen and 10 bar of acetylene were injected. After heating the autoclave to 65° C., further acetylene was injected to 20 bar. The amount of acetylene taken up at this temperature was replaced each hour for 20 h and the, after cooling, the reaction discharge was flushed with nitrogen and distilled. Dimethyl vinylphosphonate was isolated in 95 % yield.

COMPARATIVE EXAMPLE 1

Under an inert gas atmosphere 0.5 mol % dimethylphosphite, 0.5 mol % Pd (acetate)$_2$ and 0.75 mol % diphenylphosphinopropane were mixed together in a flash which was equipped with a reflux condenser. Acetylene was introduced at a rate of 6 l/h and the temperature was raised to 100° C. After 24 h the reaction mixture was chromatographically analyzed. The conversion was found to be 10% with a selectivity towards dimethylvinylphosphonate of 68% resulting in a 7% yield.

COMPARATIVE EXAMPLE 2

Under an inert gas atmosphere, 20 ml of dimethylphosphite, 80 ml of tetrahydrofuran and 1 mol % of the system of Pd (acetate)$_2$/4 triphenylphosphine/CuI were mixed together in a flask which was equipped with a reflux condenser. Acetylene was introduced at a rate of 6 l/h, and the temperature was raised to 60–80° C. After 24 h, the reaction mixture was chromatographically analyzed. The conversion was found to be 56%, with a selectivity towards dimethyl vinylphosphonate of 20%, resulting in a 11% yield.

COMPARATIVE EXAMPLE 3

The reaction was carried out as in Comparative Example 2, with BF$_3$ being used in place of CuI. The conversion was 99% with a selectivity towards diethyl vinylphosphonate of 20% (20% yield).

COMPARATIVE EXAMPLES 4–13

The reactions were carried out as in Comparative Example 2, with the following catalysts being used:

Ex
4 Pd (cyclooctadiene)Cl$_2$
5 Pd (acetate)$_2$
6 Pd (acetate)$_2$+4 triphenylphosphine
7 Pd (acetate)$_2$+4 tibutylphosphine
8 Pd (acetylacetonate)$_2$
9 Pd (triphenylphosphine)$_2$Cl$_2$
10 Pd (benzonitrile)$_2$Cl$_2$
11 Pd Cl$_2$
12 Pd I$_2$
13 Pd (CH$_3$CN)$_2$(BF$_4$)$_2$ In all cases, the desired product was formed in a yield <1%.

We claim:

1. A process for preparing a vinylphosphonic acid compound of the formula (I)

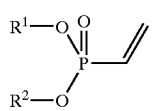  (I)

where $R^1$ and $R^2$ are, independently, H, C$_{1-16}$-aryl, C$_{7-12}$-alkaryl or C$_{7-12}$- aralkyl, it being possible for the organic radicals to be substituted by one or more halogen atoms, hydroxl, acyl, or acetoxy groups, by reacting a phosphorous compound of the formula (II)

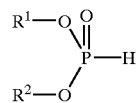  (II)

where $R^1$ and $R^2$ have the above meaning, with acetylene in the presence of 0.5 to 3% by weight of a Pd(0) complex or a Pt(0) complex as catalyst at a temperature of from 20 to 80° C.

2. A process as claimed in claim 1, wherein $R^1$ and $R^2$ are, independently, linear C$_{1-16}$-alkyl radicals.

3. A process as claimed in claim 2, wherein the ester groups are cleaved after the reaction, resulting in vinylphosphonic acid, $R^1$OH and $R^2$OH.

4. A process as claimed in claim 1, wherein a Pd(0) complex which has triarylphosphine ligands or triarylphosphite ligands is employed as catalyst.

5. A process as claimed in claim 4, wherein the complex is tetrakis(triphenylphosphine)palladium(0).

6. A process as claimed in claim 1, which has one or more of the following features:
   presence of an inert solvent
   pressure from 1 to 20 bar
   temperature from 60 to 80° C.
   amount of catalyst employed from 1 to 2% of the weight of the phosphorous acid compounds employed
   process carried out continuously.

7. A process for preparing a vinylphosphonic acid compound of the formula (I)

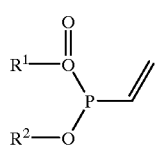  (I)

where $R^1$ and $R^2$ are independently, H, C$_{1-16}$-alkyl, C$_{6-12}$-alkaryl or C$_{7-12}$-arakyl, it being possible for the organic radicals to be substituted by one or more halogen atoms, hydroxyl, acyl or acetoxy groups, by reacting a phosphorous compound of the formula (II)

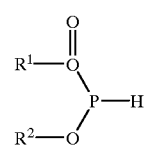  (II)

where $R^1$ and $R^2$ have the above meaning, with acetylene in the presence of 0.5 to 3% by weight of tetrakis (triphenylphosphine)palladium(0) as catalyst at a temperature of from 60 to 80° C.

* * * * *

UNITED STATES PATENT AND TRADEMARK OFFICE
CERTIFICATE OF CORRECTION

PATENT NO.    : 6,479,687 B1
DATED         : November 12, 2002
INVENTOR(S)   : Henkelmann et al.

It is certified that error appears in the above-identified patent and that said Letters Patent is hereby corrected as shown below:

<u>Title page,</u>
Item [57], ABSTRACT,
Penultimate line, "complexe" should be -- complex --.

Signed and Sealed this

Twenty-fifth Day of February, 2003

JAMES E. ROGAN
*Director of the United States Patent and Trademark Office*